United States Patent [19]
Carter et al.

[11] Patent Number: 5,989,540
[45] Date of Patent: Nov. 23, 1999

[54] MODIFIED ADENO-ASSOCIATED VIRUS VECTOR CAPABLE OF EXPRESSION FROM A NOVEL PROMOTER

[75] Inventors: Barrie J. Carter, Kensington; Terence Flotte, Baltimore; Sandra Afione, Bethesda; Rikki Solow, Gaithersburg, all of Md.

[73] Assignee: The United States of America as represented by the Department of Health & Human Services, Washington, D.C.

[21] Appl. No.: 08/455,231

[22] Filed: May 31, 1995

Related U.S. Application Data

[62] Division of application No. 07/891,962, Jun. 2, 1992, Pat. No. 5,587,308.

[51] Int. Cl.$^6$ .................... A61K 48/00; C12N 15/64; C12N 15/86
[52] U.S. Cl. .................... 424/93.2; 424/93.6; 435/69.1; 435/455; 435/456; 435/320.1
[58] Field of Search .................... 435/69.1, 320.1, 435/455, 456; 424/93.1, 93.2, 93.6

[56] References Cited

U.S. PATENT DOCUMENTS 4,797,368   1/1989   Carter et al. ....................... 435/320.1

OTHER PUBLICATIONS

Nabel et al., Science, vol. 249, pp. 1285–1288, Sep. 14, 1990.
Wolff et al., Science, vol. 247, pp. 1465–1468, Mar. 23, 1990.
Rosenfeld et al., Science, vol. 252, pp. 431–434, Apr. 19, 1991.
Wu et al., J. Biol. Chem., vol. 263, No. 29, pp. 14621–14624, Oct. 15, 1988.
Nicolau et al., PNAS, vol. 80, pp. 1068–1072, Feb. 1983.
Kaneda et al., Science, vol. 243, pp. 375–378, Jan. 20, 1989.
Benvenisz et al., PNAS, vol. 83, pp. 9551–9555, Dec. 1985.
Seeger et al., PNAS, vol. 81, pp. 5849–5852, Sep. 1984.
Dubensky et al., PNAS, vol. 81, pp. 7529–7533, Dec. 1984.
Mannino et al., BioTechniques, vol. 6, No. 7, pp. 682–690, 1988.
Conrad et al., Gene Therapy, vol. 3, pp. 658–668, 1996.
Afione et al., J. of Virol., vol. 70, No. 5, pp. 3235–3241, May 1996.
Flotte et al., Human Gene Therapy, vol. 7, pp. 1145–1159, Jun. 10, 1996.
Flotte, et al., Pediatric Pulmonary, Supplement 13, abstract, #239, Sep. 1996.
Wagner et al., Pediatric Pulomonary, Supplement 13, abstract #239, Sep. 1996.
Barrie J. Carter, Nature Biotechnology, vol. 14, pp. 1725–1726, Dec. 1996.
Bartlett et al., Genetics and Biology of Adeno–Associated Virus, in Chapter 4, pp. 55–73, of "Visual Vectors", Academic Press, 1995.
Verma et al., Nature, vol. 389, pp. 239–242, Sep. 18, 1997.
Orkin et al., "Report and Recommendations of the Panel to Assess the NIH Investment in Research on Gene Therapy", Dec. 7, 1995.
Marshall, "Gene Therapy's Growing Pains", Science, vol. 269, Aug. 25, 1995, pp. 1050–1055.
Kotin, "Prospects for the Use of Adeno–Associated Virus as a Vector for Human Gene Therapy", Human Gene Therapy, vol. 5, pp. 793–801, 1994.
Wickens et al. "Role of the Conserved AAVAAA Sequence: Four AAVAAA Point Mutants Prevent Messenger RNA 3' End Formation," Science 226:1045–1051 (1984).
Susan K. McLaughlin et al., "Adeno–Associated Virus General Transduction Vectors: Analysis of Proviral Structures," Journal of Virology, 62(6):1963–1973 (Jun. 1988).
Beaton et al., "Expression from the Adeno–Associated Virus p5 and p19 Promoters is Negatively Regulated in trans by the rep Protein," Journal of Virology 63:4450–4454 (1989).
Riordan et al., "Identification of te Cystic Fibrosis Gene: Cloning and Characterization of Complimentary DNA," Science 245:1066–1073 (1989).
Collins et al., "Cystic Fibrosis: Moloecular Biology and Therapeutic Implications" Science 256: 774–779 (1992).
Srivastava et al. "Construction of a Recombinant Human Parvovirus B19: Adeno–Associated Virus 2 (AAV) DNA Inverted Terminal Repeats are Functional in an AAV–b19 Hybrid Virus," Proc. Natl. Acad. Sci. 86:8078–8082, Oct. 1989.
Rosenfeld et al. "In Vitro Transfer of the Human Cystic Fibrosis Transmembrane Conductance Regulator Gene to the Sarrows Epathelum" Cell, vol. 68, pp. 143–155, Jan. 10, 1992.

*Primary Examiner*—David Guzo
*Attorney, Agent, or Firm*—Needle & Rosenberg, P.C.

[57] ABSTRACT

Described herein are constructions of recombinant DNA comprising modified adeno-associated virus (AAV) DNA sequences capable of functioning as a eukaryotic expression vector for expressing foreign DNA sequences using a novel transcription promoter comprising the termini of AAV DNA. It is shown that expression of a test reporter gene can be obtained from this vector in mammalian cells. It is further shown that this combination of vector and promoter can be used to introduce and express a human gene and correct a genetic defect in human cells resulting from malfunction of the mutant endogenous gene. Further, the vector can be used to correct the genetic defect by expressing a modified version of the human gene consisting of a fusion of part of the said gene and a synthetic sequence contained in the vector.

7 Claims, 6 Drawing Sheets pSA 313 pSA 315 pSA 306 pSA 464

5,989,540

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
         (A) LENGTH: 58 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

CAGGCCTAAT AAAGAGCTCA GATGCATCGA TCAGAGTGTG TTGGTTTTTT GTGTGTAC         58

(2) INFORMATION FOR SEQ ID NO:2:

(i) SEQUENCE CHARACTERISTICS:
         (A) LENGTH: 62 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

GTACACACAA AAACCAACA CACTCTGATC GATGCATCTG AGCTCTTTAT TAGGCCTGGT        60

AC                                                                     62

(2) INFORMATION FOR SEQ ID NO:3:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

AGCTGGTCTT TGGCATTAGG AGCTTGAGCC CAGACGGCCC TAGCAGGGAC CCCA             54

(2) INFORMATION FOR SEQ ID NO:4:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:

AGCTTGGGGT CCCTGCTAGG GCCGTCTGGG CTCAAGCTCC TAATGCCAAA GACC             54

(2) INFORMATION FOR SEQ ID NO:5:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

AGCTCAGACG GCCCTAGCAG GGACCCA                                       27

(2) INFORMATION FOR SEQ ID NO:6:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:6:

AGCTTGGGTC CCTGCTAGGG CCGTGTC                                       27

(2) INFORMATION FOR SEQ ID NO:7:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:7:

GTGACGTGAA TTACGTCATA G                                             21

(2) INFORMATION FOR SEQ ID NO:8:

(i) SEQUENCE CHARACTERISTICS:
       (A) LENGTH: 12 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:8:

AACTCCATCA CT                                                       12

(2) INFORMATION FOR SEQ ID NO:9:

(i) SEQUENCE CHARACTERISTICS:
       (A) LENGTH: 12 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:9:

GGCCGCCCGG GC                                                       12

(2) INFORMATION FOR SEQ ID NO:10:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:10:

AAAGCCCGGG CGTCGGGCGA CC                                            22

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGTCGCCCGG CCTCA                                                            15

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGCGGCGAG AG                                                                12

(2) INFORMATION FOR SEQ ID NO:13:

(i) SEQUENCE CHARACTERISTICS:
        (A) LENGTH: 58 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

CAGGCCTAAT AAAGAGCTCA GATGCATCGA TCAGAGTGTG TTGGTTTTTT GTGTGTAC       58

MODIFIED ADENO-ASSOCIATED VIRUS VECTOR CAPABLE OF EXPRESSION FROM A NOVEL PROMOTER

This application is a divisional of application Ser. No. 07/891,962, filed Jun. 2, 1992, now U.S. Pat. No. 5,587,308.

BACKGROUND OF THE INVENTION

Adeno-associated virus (AAV) usually is defective for replication and depends on co-existent adenovirus or herpesvirus infection for efficient replication and a productive life cycle. In the absence of helper virus, AAV can undergo stable integration of its genome into the host cell but the integrated AAV genome has no pathogenic effect. These properties formed the basis for the development of AAV vectors for gene expression in mammalian cells. AAV vectors have been used to express both selective markers (Hermonat and Muzyczka, 1981, *Proc. Natl. Acad. Sci. USA* 81:6466–6470; Tratschin et al., 1985, *Mol. Cell. Biol.* 5:3251–3260) such as neomycin phosphotransferase (neo) and unselected genes including chloramphenicol acetyltransferase (cat) (Tratschin et al., 1984, *Mol. Cell. Biol.* 4:2072–2081) and thyroid stimulating hormone in eukaryotic cells (Mendelson et al., 1988, *Virology* 166:154–165; Wondisford et al., 1988, *Molec. Endocrinol.* 2:32–39).

For use as a viral transducing vector AAV may present some advantages including a high frequency of stable DNA integration and the lack of pathogenicity of wild type AAV. One limitation of AAV is that of size, since the packaging limit for foreign DNA in AAV particles is approximately 4.5 kilobases. This limitation is an important consideration for the design of AAV vectors for expression of genes or cDNA constructs in which the gene coding sequence approaches that of the AAV packaging limit, i.e., approximately 4.5 kilobases.

One such gene, for example, is the cystic fibrosis gene (CFTR). The airway epithelium is a critical site of cellular dysfunction in cystic fibrosis (CF), the most common lethal genetic disease in North America, and is characterized by a defect in regulation of Cl⁻ conductance (Hwang et al., 1989, *Science* 244:1351–1353; Li, et al., 1988, *Nature* (London) 331:358–360, Li et al., 1989, *Science* 244:1353–1356; Schoumacher et al., 1987, *Nature* (London) 330:752–754). The cDNA for the CFTR gene (Riordan et al., 1989, *Science* 245:1066–1073; Rommens et al., 1989, *Science* 245:1059–1065) has been expressed in eukaryotic cells. Expression of the CFTR protein in non-epithelial cell lines resulted in generation of a Cl⁻ conductance (Andersen et al., 1991, *Science* 251:679–682; Kartner et al., 1991, *Cell* 64:681–691). The CF defect has been complemented by expression of CFTR in a CF pancreatic adenocarcinoma cell line by stable transduction with a retrovirus vector (Drumm et al., 1990, *Cell* 62:1227–1233), and in a CF airway cell line by infection with a vaccinia virus (Rich et al., *Nature* (London) 347:358–363) or an adenovirus vector (Rosenfeld et al., 1992, *Cell* 68:143–155).

Gene therapy has been proposed as a way to reverse the cellular defect and prevent progression of disease in affected patients. Previous approaches to gene therapy have involved in vitro transduction of cells (such as lymphocytes) which can be easily reintroduced into patients. This may be difficult in an intact respiratory epithelium. An alternative approach is to use a virus vector to deliver the CFTR gene directly to the airway surface. One candidate is adeno-associated virus (AAV), a human parvovirus. The coding sequence (Riordan et al., 1989, *Science* 245:1066–1073) of CFTF, however, is 4.4 kilobases, which approaches the packaging limit of AAV particles. Thus, AAV has a potential drawback for its use as a vector for CFTR in that it barely accommodates the coding sequence of CFTR (Collins, 1992, *Science* 256:774–779).

AAV transducing vectors are described in the patent of Carter et al., (U.S. Pat. No. 4,797,368, issued Jan. 10, 1989). This patent describes AAV vectors using AAV transcription promoters $P_{40}$, $P_{19}$ and $P_5$.

AAV vectors must have one copy of the AAV inverted terminal repeat sequences (ITRs) at each end of the genome in order to be replicated, packaged into AAV particles and integrated efficiently into cell chromosomes. The ITR consists of nucleotides 1 to 145 at the left end of the AAV DNA genome and the corresponding nucleotides 4681 to 4536 (i.e., the same sequence) at the right hand end of the AAV DNA genome. Thus, AAV vectors must have a total of at least 300 nucleotides of the terminal sequence.

For packaging large coding regions, such as the CFTR gene into AAV vector particles, it is important to develop the smallest possible regulatory sequences, such as transcription promoters and polyA addition signal. Also in this latter study and another study (Beaton et al., 1981, *J. Virol.* 63:4450–4454) it was shown that the AAV ITR sequence can act as an enhancer for the SV40 virus early gene transcription promoter. However, it was not shown that the AAV ITR region had any intrinsic transcription promoter activity. Indeed, it is taught in the literature that the AAV ITR regions have no transcriptional function (Walsh et al., 1992, *PNAS* [in press]). Therefore, in the previous AAV vectors a small transcription promoter was utilized, namely the AAV $P_5$ promoter, which consists of nucleotides 145 to 268 of the AAV genome positioned immediately adjacent to an ITR.

Thus, there exists a need to increase the packaging size of AAV while maintaining efficient expression. The present invention satisfies this need by showing that a gene can be functionally expressed from an AAV vector when it is positioned adjacent to the AAV ITR even in the absence of another promoter. This finding demonstrates a previous unrecognized ability of AAV termini to function as fully competent transcription promoters. This demonstrates that AAV vectors can be constructed in which the ITR itself is acting as the transcription promoter and no other promoter sequences must be incorporated into the vector. It is also shown that a CFTR fusion gene consisting of the CFTR cDNA and a synthetic oligonucleotide positioned in an AAV vector immediately adjacent to an AAV ITR can be functionally expressed in human cells to correct the cystic fibrosis defect.

SUMMARY OF THE INVENTION

This invention provides an adeno-associated viral vector comprising the inverted terminal repeat sequences of adeno-associated virus and a nucleic acid, wherein the promoter sequence of the inverted terminal repeat sequences promotes expression of the nucleic acid in the absence of another promoter. Also provided is an isolated nucleic acid consisting essentially of the promoter sequence of the inverted terminal repeat sequences of adeno-associated virus. Methods utilizing these sequences are also provided.

Figure 2:
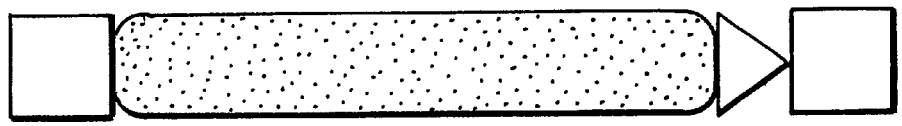
Figure 2:
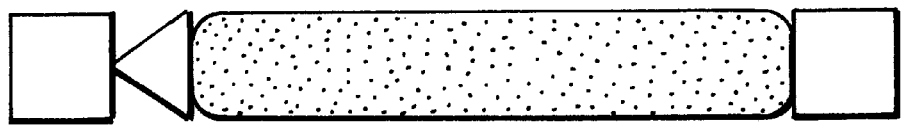
Figure 2:
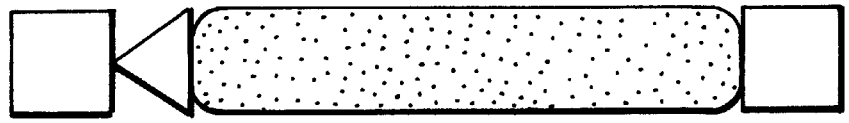
Figure 2:
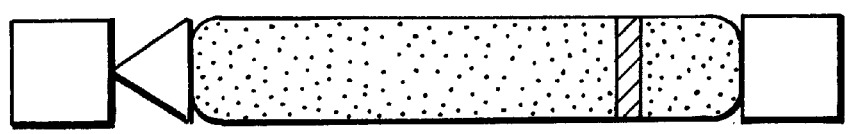

FIG. 2 shows the structure of the AAV-CFTR vector plasmids as indicated. pSA313 contains the CFTR cDNA (indicated by the cross-hatched region and arrow head) inserted downstream of the AAV $P_5$ promoter (i.e., at nucleotide 266) and contains the synthetic polyA site. pSA315 has the same CFTR insert as pSA313 in the same plasmid but the inserted CFTR cDNA is inserted in the opposite direction and is expressed from the right-hand AAV ITR promoter. pSA306 is the same as pSA313 except for a deletion of nucleotides 131 to 486 from the CFTR sequence. pSA464 is the same as pSA306 except that a frameshift mutation was introduced at an AflII site at nucleotide 993 in the CFTR sequence as indicated by the vertical solid bar.

FIG. 3(A–D) shows Cl⁻ efflux assays in airway epithelial cells complemented with the CFTR gene by stable transfection of an AAV-CFTR vector. Individual panels show Cl⁻ efflux in IB3-1 (FIG. 3A) cells or IB3-N6, (FIG. 3B) IB3-C38 (FIG. 3C) and I3-C35 (FIG. 3D) cells as indicated. IB3-N6 is a clone of IB3 stably transfected with the AAVp₅neo vector alone, whereas the C38 and C35 clones were derrved from IB3 cells stably transfected with pAAVp₅neo plus pSA306 as described in the text. Efflux was measured in the absence (0) or presence (⊚) of 20 uM forskolin.

Figure 4:
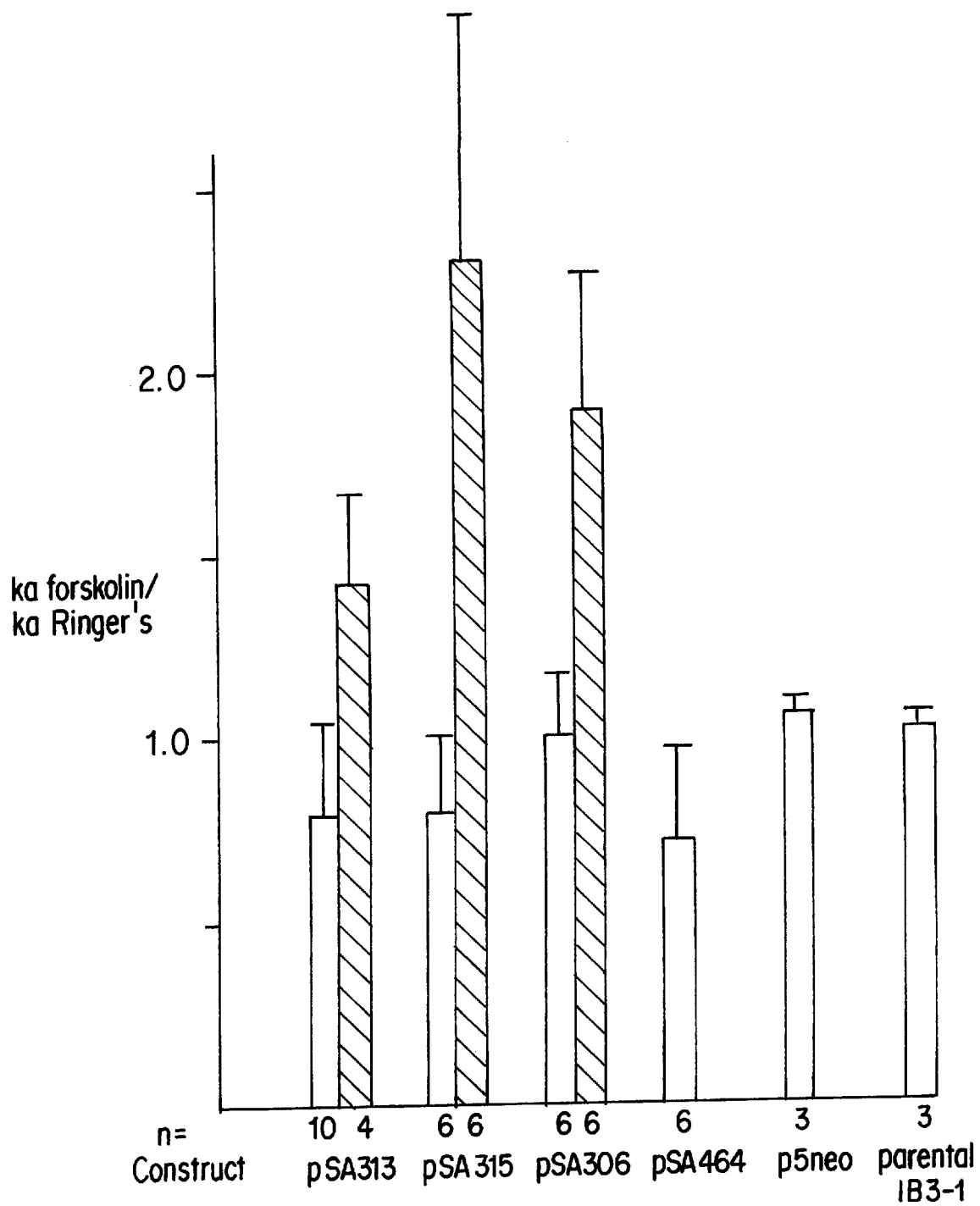

FIG. 4 shows Cl⁻ efflux assays in IB3-1 cells complemented with the CFTR gene by stable transfection of AAV-CFTR vectors. IB-3 cells were transfected with pAAVp₅neo and either pSA313, pSA315, pSA306, or pSA464. Geneticin-resistant clones were selected and analyzed for responsive to forskolin stimulation in a Cl– efflux assay. The ratio of the rate of efflux in the presence of forskolin to the rate in the absence of forskolin ($k_a$ forskolin/$k_a$ Ringer's) is plotted. For each vector, n indicates the number of individual clones which did (hatched bars) or did not (open bars) show a forskolin response. For each group of clones the average ratio was calculated. For the parental IB3-1 cells or the cell clone transfected with the pAAVp₅neo alone, n indicates the number of measurements on the same clone.

Figure 5:
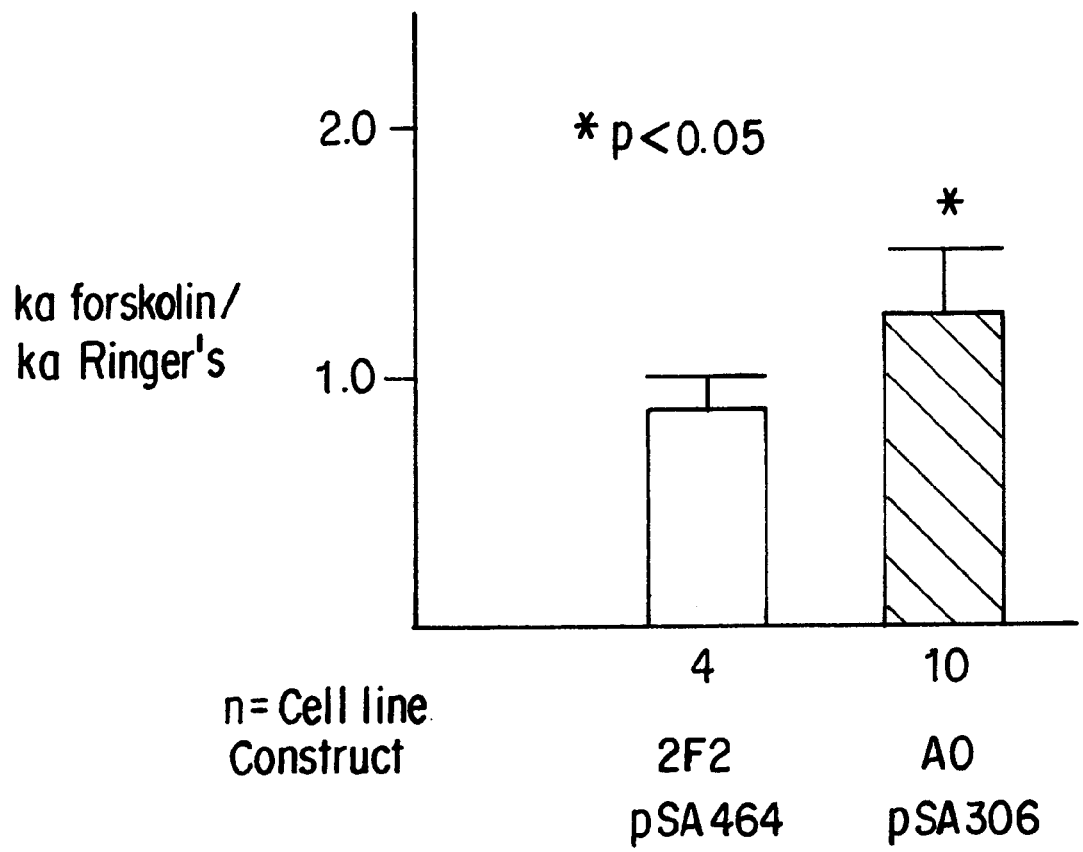

FIG. 5 shows transduction of IB3 cell cultures with the AAV-CFTR vectors. The AAV-CFTP vectors in pSA306 or pSA464 were packaged into AAV particles as described were then used to infect IB3 cells at a multiplicity of approximately 300 to 400 particles per cell. The cultures were passaged for several weeks and then tested for complementation of the CF defect in the Cl⁻ efflux assay. The culture A0 was complemented by the SA306 transducing vector whereas the culture 2F2 was not complemented by the mutant SA464 vector.

DETAILED DESCRIPTION OF THE INVENTION

This invention provides that the AAV ITR is independently able to influence gene expression. This reflects a previously unrecognized ability of AAV ITR to function as a fully competent transcription promoter. This is proven by constructing an AAV vector in which the reporter gene, cat, is linked directly to the ITR and is expressed when introduced into cells.

AAV vectors containing the full length CFTR cDNA are larger than wild type AAV and are difficult to package into AAV transducing particles. However, the invention provides that a CFTR cDNA expressed from an AAV ITR promoter is able to complement the CF defect and is regulated appropriately as indicated by functional assays. The invention also demonstrates that this truncated CFTR cDNA could be packaged into an AAV vector and infected into IB3 cells such that the bulk culture could be complemented for the CF defect. Therefore, the invention provides that it is possible to obtain efficient complementation of the CF defect with AAV transducing vectors.

Therefore, the present invention provides an adeno-associated viral vector comprising the inverted terminal repeat (ITR) sequences of adeno-associated virus and a nucleic acid, wherein the inverted terminal repeat sequences promote expression of the nucleic acid in the absence of another promoter. By "adeno-associated viral vector" is meant any vector which has the ITR sequences necessary to package the viral genome, integrate into a host chromosome and promote transcription of additional sequences. Thus, any changes in the ITR which retain these essential functions is considered within the meaning of ITR.

The nucleic acid promoted by ITR can be any desired sequence. In one embodiment, the nucleic acid can encode a polypeptide which has a desired function in the cell in which the vector is expressed. For example, the polypeptide can be a protein having a desired function in a cell, on the surface of the cell, or when secreted. One example of a protein is CFTR. As described above and in more detail below, the vector is ideally suited for larger nucleic acids, like CFTR, which approach the maximum packaging size for standard AAV vectors and for therapy purposes should be integrated into the genome. Alternatively, the nucleic acid sequence simply can encode an antisense RNA for use in antisense related therapy.

The viral vector can be contained in a suitable host. Any cell can be a suitable host so long as the vector is capable of infecting the cell type. One example of a suitable host is an epithelial cell containing a non-functional CFTR sequence for use when the vector contains a functional CFTR sequence.

The vector can contain additional sequences, such as from adenovirus, which aid in effecting a desired function of the vector. For example, the addition of adenovirus DNA sequences enclosing the AAV vector could provide an approach to packaging AAV vectors in adenovirus particles.

The vector can also be contained in any pharmaceutically acceptable carrier for administration or the like. Examples of suitable carriers are saline or phosphate buffered saline.

As used herein, AAV means all serotypes of AAV. Thus, it is routine in this art to use the ITR sequences from other serotypes of AAV since the ITRs of all AAV serotypes are expected to have similar structures and functions with regard to replication, integration, excision and transcriptional mechanisms.

The invention provides a method of delivering a protein to a subject comprising infecting the subject with the vector of the invention. While not limited to humans, most therapy uses of the vector will be applicable mainly to humans. In this regard, the invention provides a method of delivering a functional cystic fibrosis transmembrane conductance regulator to a human subject comprising infecting the subject with the CFTR containing vector of the invention. This method thus can be utilized to treat cystic fibrosis.

Also provided is an isolated nucleic acid consisting essentially of the inverted terminal repeat sequences of adeno-associated virus. In addition, the invention provides a vector comprising this nucleic acid provided the vector is not an adeno-associated virus vector. This vector can be contained in a suitable host and in a pharmaceutically acceptable carrier. Thus, as described in more detail below, the specific promoter sequences can be determined and utilized to promote expression in other vectors.

The invention also provides a vector comprising a polyA site that is capable of being translationally read in the reverse direction. The specific sequence disclosed below can be modified by standard procedures and still maintain this capability.

The invention also discloses a viral vector comprising a polyA site that is capable of being translationally read in the reverse direction; the ITRs of adeno-associated virus; and a nucleic acid encoding a polypeptide. In this vector, the inverted terminal repeat sequences promote expression of the nucleic acid in the absence of another promoter. Thus, this vector has the advantages of maximum packaging capabilities and the capability to be read in the reverse direction.

Finally, a functional cystic fibrosis transmembrane conductance regulator protein having a deletion of the amino terminal sequence is provided. While the particular deletion disclosed is in amino acids 1 through 118, the invention provides the first documentation of an amino terminal deletion which maintains function. Given this discovery, it would be routine to delete various alternative amino terminal deletions to accomplish the same purpose by following the methods set forth below.

Experimental Procedures and Results

Cells

The CFBE IB3-1 cell line (IB3 cells) is a human bronchial epithelial cell line derived from a CF patient and immortalized with an adeno/SV40 hybrid virus (Luo et al., 1989, *Pflugers Arch.* 415:198–203; Zeitlin et al., 1991, *Am. J. Respir. Cell Mol. Biol.* 4:313–319). These cells retain characteristics of epithelial cells and are deficient in protein kinase A activation of chloride conductance. IB3 cells were grown at 37° C. in 5% $CO_2$ in LHC-8 medium (Biofluids, Inc. Md) plus 10% fetal calf serum with added endothelial cell growth supplement (15 ug/ml) in culture flasks or dishes coated with collagen (150 ug/ml), fibronectin (10 ug/ml) and bovine serum albumin (10 ug/ml). The 293-31 cell line (293 cells), originally derived from human embryonic kidney cells transformed with the adenovirus type 5 E1A and E1B genes, were grown at 37° C. in 5% $CO_2$ in Eagle's Minimal Essential Medium with 10% fetal calf serum and were used for transfection assays of cat vectors and for packaging AAV vectors into virus particles (Tratschin et al., 1984, *Mol. Cell. Biol.* 4:2072–2081).

Plasmids

Plasmids were constructed and grown using standard methods (Sambrook et al., 1989, *Molecular Cloning*, Cold Spring Harbor Laboratory, Cold Spring Harbor, N.Y.). The AAV-cat plasmids were constructed as follows. The parental plasmid, pAV2, contains the entire 4681 nucleotide sequence of AAV2 inserted in a pBR322 derived plasmid via a polylinker and BglII linkers (Laughlin et al., 1983, *Gene* 23:681–691). From this a plasmid pYT45 was obtained which contained a prokaryotic cat gene immediately downstream of AAV nucleotides 1 to 263 (which placed the cat gene under control the AAV $p_5$ promoter) followed by AAV nucleotides 1882–1910 and 4162–4681 (containing the polyA signal and right hand ITR) downstream of the cat gene.

pRO1472 was derived from pYT45 by first deleting a SnaBI/NdeI fragment (AAV nucleotide 4498 to pBR322 nucleotide 2295) to yield pRO45. This removed the right hand AAV ITR but retained the AAV polyadenylation (polyA) site downstream of the cat gene. pRO1472 was then constructed by insertion of a synthetic double-stranded oligonucleotide into the HindIII site of pRO45. The oligonucleotide consisted of AAV nucleotides 266–321 flanked by HindIII overhangs such that only the 5' end of the insert had a complete HindIII site after ligation. Proper insertion was confirmed by sequencing. The final construct pRO1472 contains AAV nucleotides 1–321 upstream of the cat gene (except that nucleotides 264 and 265 are changed from the wild type sequence CC to TT) and AAV nucleotides 1882–1910 and 4162–4492 (containing the polyA signal) downstream.

pSA60 was derived from pYT45.1 (which is a derivative of pYT45 obtained by filling in (i.e., inactivating) the BamH-I site in the poly-linker sequence immediately upstream of the left-hand ITR) by cleaving pYT45.1 with KpnI and SnaB to remove the region containing the AAV polyA signal (AAV nucleotides 4162 to 4495) and inserting a 60 base-pair synthetic oligonucleotide (SPA) containing a synthetic polyA site (modified from Levitt et al., 1989, *Genes and Development* 3:1019–1025) having KpnI and SnaB compatible termini. This SPA was obtained by synthesizing two single oligonucleotides having the following sequences:

5'-CAGGCCTAATAAAGAGCTCAGATGCATCGATCAGAGTGTGTTGGTTTTTTGTGTGTAC-3'     [SEQ ID NO1]

and

5'-GTACACACAAAAAACCAACACACTCTGATCGATGCATCTGAGCTCTTTATTAGGCCTGGTAC-3'     [SEQ ID NO2]

and annealing these two oligonucleotides to generate the 60 base-pair nucleotide with KpnI and SnaB compatible termini. This SPA was designed such that in the sense direction it is a functional polyA site and in the other orientation it can be translated through as an open reading frame. The presence of the SPA in pSA60 was verified by DNA sequencing.

pSA665 was derived from pSA60 by inserting at the HindIII site a 54 base-pair oligonucleotide (representing the 54 bases upstream of the initiation codon of the CFTR gene, i.e., nucleotides aa to bb in the CFTR sequence of Drumm et al., 1990) via a HindIII site at one end and a HindIII compatible site at the other. This 54 base oligonucleotide was derived by synthesizing and annealing the two oligonucleotides:

5'-AGCTGGTCTTTGGCATTAGGAGCTTGAGCCCAGACGGCCCTAGCAGGGACCCCA-3' [SEQ ID NO3]

and

5'-AGCTTGGGGTCCCTGCTAGGGCCGTCTGGGCTCAAGCTCCTAATGCCAAAGACC-3' [SEQ ID NO4].

pSA673 was derived in a similar fashion except that the inserted oligonucleotide contained only 27 nucleotides of the upstream CFTR sequence (i.e., CFTR cDNA nucleotides aa to bb).

The 27 base-pair oligonucleotide was derived by synthesizing and annealing the two 27 base oligonucleotides:

5'-AGCTCAGACGGCCCTAGCAGGGACCCA-3' [SEQ ID NO5]

and

5'-AGCTTGGGTCCCTGCTAGGGCCGTGTC-3' [SEQ ID NO6].

The presence of the inserted oligonucleotides were verified by sequencing.

pTRF46 was derived by generating via the PCR reaction a 842 base-pair fragment of pRO1472 comprising the region from the pBR322 PvuI site to the nucleotide 145 of the AAV ITR using primers that gave a PvuI site in the pBR322 region and a HindIII site adjacent to the AAV ITR. This was then inserted into pSA60 that had been cleaved with PvuI and HindIII. The effect of these operations was to generate pTRF46 that is identical to pSA60 except that it is deleted for nucleotides 146 to 263 of AAV (i.e., the entire $p_5$ promoter) and places the cat coding region adjacent to the AAV ITR. The sequence of the entire AAV ITR region and junction with the cat sequence in pTRF46 was verified by DNA sequencing.

pAAVp$_5$neo is analogous to pYT45 except that it has a neo coding sequence in place of the cat gene and the downstream AAV nucleotides 1882–1910 and 4162–4492 (the KpnI/SnaB fragment) were replaced 60 bp SPA.

pSA313 is analogous to pAAVp$_5$neo except that the neo sequence was replaced with the CFTR coding sequence contained in a 4502 bp AvaI-SstI fragment excised from a plasmid pBA-CFTRBQ (Drumm et al., 1990, *Cell* 62:1227–1233). This CFTR cDNA sequence contains the three silent point mutations in exon 6a which eliminate the prokaryotic promoter sequence. In pSA313, the CFTR gene is under control of the AAV $p_5$ promoter. The plasmid pSA315 is analogous to pSA313, except that the CFTR cDNA is inserted in the opposite direction. The plasmid pSA306G is analogous to pSA315 except that it has a deletion of the CFTR nucleotides 131 to 486. In both pSA315 and pSA306 the CFTR gene is expressed from the AAV ITR as discussed below. The junction sequences between the CFTR insert and the AAV termini and SPA regions of pSA313, pSA315, and pSA306 were verified by DNA sequencing. pSA464 was derived from pSA306 by cleaving with AflII at nucleotide of the CFTR sequence and filling in and blunt-end ligation with T4 DNA polymerase and T4 DNA ligase. This generated a frameshift in the CFTR sequence. The presence of this mutation was verified by DNA sequencing.

Transfection

DNA transfection in IB3 was performed in 6- or 24-well dishes using lipofection. Thirty ug of lipofection reagent (BRL, Gaithersburg, Md.) was used for each 5 to 6 ug of DNA transfected. Lipofectin and DNA were mixed in 1.0 ml of LHC-8 serum-free medium and added to cells ($5\times10^5$ to $5\times10^6$ in 35 mm wells) already covered with 0.5 ml of medium. Cells were exposed to DNA for 4 hours, rinsed with PBS and then grown in 2 ml of fresh medium. DNA transfection in 293 cells was performed by the standard DNA-calcium phosphate precipitation procedure.

Geneticin Selection

IB3 cells used for stable neo expression were split 1:3 into 10 cm dishes at 24 to 48 hours after transfection and geneticin sulfate was added 72 to 96 hours after transfection at a concentration of 120 ug/ml. The amount of geneticin used was based on a minimal lethal dose titration. Geneticin resistant (gen$^r$) colonies were counted at 14 to 16 days after beginning selection.

CFTR Complementation

IB3 cells were plated at approximately $5\times10^5$ cells 35 mm dish. Twenty-four hours after plating, cells were transfected using either 6 ug of pAAVp$_5$neo or 1 ug of pAAVp$_5$neo together with 5 µg of pSA313, pSA315, pSA306, or pSA464 by lipofection, and geneticin selection was performed as described above.

Gen$^r$ colonies were isolated at 14 days after beginning selection from each of the other two sets of plates. Each isolated colony was trypsinized using a cloning cylinder and expanded from 10 mm wells. After expanding each clone, cells were prepared for $^{36}$Cl$^-$ efflux assays and Western blot analysis.

Chloride Efflux Assays

Chloride efflux assays were performed as described (Trapnell et al., 1991, *J. Biol. Chem.* 266:10319–10323) on individual clones at passage 4 to 8. Briefly, cells were grown in 35 mm dishes and loaded with 3 uCi of $^{36}$Cl$^-$ in bicarbonate-free Ringer's balanced salt solution for 2 to 9 hours. Initial experiments involving repeated assays on the same clone of cells did not reveal significant differences in efflux following different loading times and a 2 hr loading period was then used for subsequent experiments. After loading the cells were washed 2 to 3 times in ice cold 0.15 M NaCl, 5 mM Hepes, pi 7.4. One ml of Ringer's solution was added and removed immediately (time zero) and replaced with 1 ml of Ringer's. This process was repeated at various time points over a 15 min period. The amount of radioactivity in each 1 ml sample of medium was determined by liquid scintillation counting. After the last sample was removed at 15 min, residual radioactivity remaining in the cells was determined by lysing the cells in 0.2 N NaOH and scintillation counting. The total radioactivity from all time points and the final cell lysate was then summed and the efflux was expressed as a percent of total radioactivity remaining in the cells at each time point. Effluxes were then repeated for each clone tested, using 10 uM forskolin dissolved in the Ringer's efflux solution, starting at time zero. The relative stimulation by forskolin was then expressed by calculating the rate ($k_a$) of efflux in the presence of forskolin and expressing this as a ration relative to the rate of efflux in the absence of forskolin. For IB3 cells which exhibit the CF defect this ratio is 1.0 or less. For cells complemented by CFTR vectors this ration is greater than 1.0.

Cat Assays

Cells used for transient expression of cat vectors were harvested at 48 hours after transfection, lysed by three cycles of freezing and thawing, and assayed for cat activity (Tratschin et al., 1984, *Mol. Cell. Biol.* 4:2072–2081).

Packaging Of AAV2-CFTR Vectors

Packaging of AAV2 vectors was accomplished by first infecting 293-31 cells (grown to semiconfluence in 100 mm dishes) with adenovirus type 5 (Ad5) (at a multiplicity of 5 to 10 infectious units/cell) and then co-transfecting the vector plasmid, pSA306 or pSA464 (1 μg) and the packaging pAAV/Ad (5 μg) using the $CaPO_4$ transfection procedure (Tratschin et al., 1984, *Mol. Cell. Biol.* 4:2072–2081). Medium was replaced 2 hr prior to transfection and Ad5 was inoculated into the medium 1 hr prior to transfection. The medium was changed 4 hr after transfection. Cells were grown for 3 to 4 days then harvested by gently scraping into the medium. For direct analysis of packaging, the lysates were frozen and thawed three times, debris was removed by low speed centrifugation, then heated at 60° C. for 15 min to inactivate adenovirus. For use of vectors in transduction of IB3 cells the scraped cells were concentrated by low-speed (4000 rpm) centrifugation and resuspension in 10 mM Tris-HCl buffer, pH 8.0. Cells were lysed by freezing and thawing three times and the virus was concentrated and purified using CsCl density gradient ultracentrifugation (Carter et al., 1979, *Virology* 92:449–462). Fractions taken for transduction assays were then dialyzed against 1×SSC three times for 1 h at room temperature and heat-treated at 60° C. for 15 minutes to inactivate any possible residual adenovirus. The titer of the vector preparation was determined by DNA slot-blot hybridization (Samulski et al., 1989, *J. Virol.* 63:3822–3828).

AAV2-Particle Mediated Transduction

Virus particle-mediated neo transduction of IB3-1 CF bronchial epithelial cells was accomplished by infecting $10^3$ to $4×10^4$ cells in individual wells of a 24 well dish with a known number of AAV-CFTR vector particles per cell. The cells were grown for several weeks and assayed for complementation of the CF defect.

Activity Of The AAV $p_5$ Promoter Based Vectors

Figure 1:
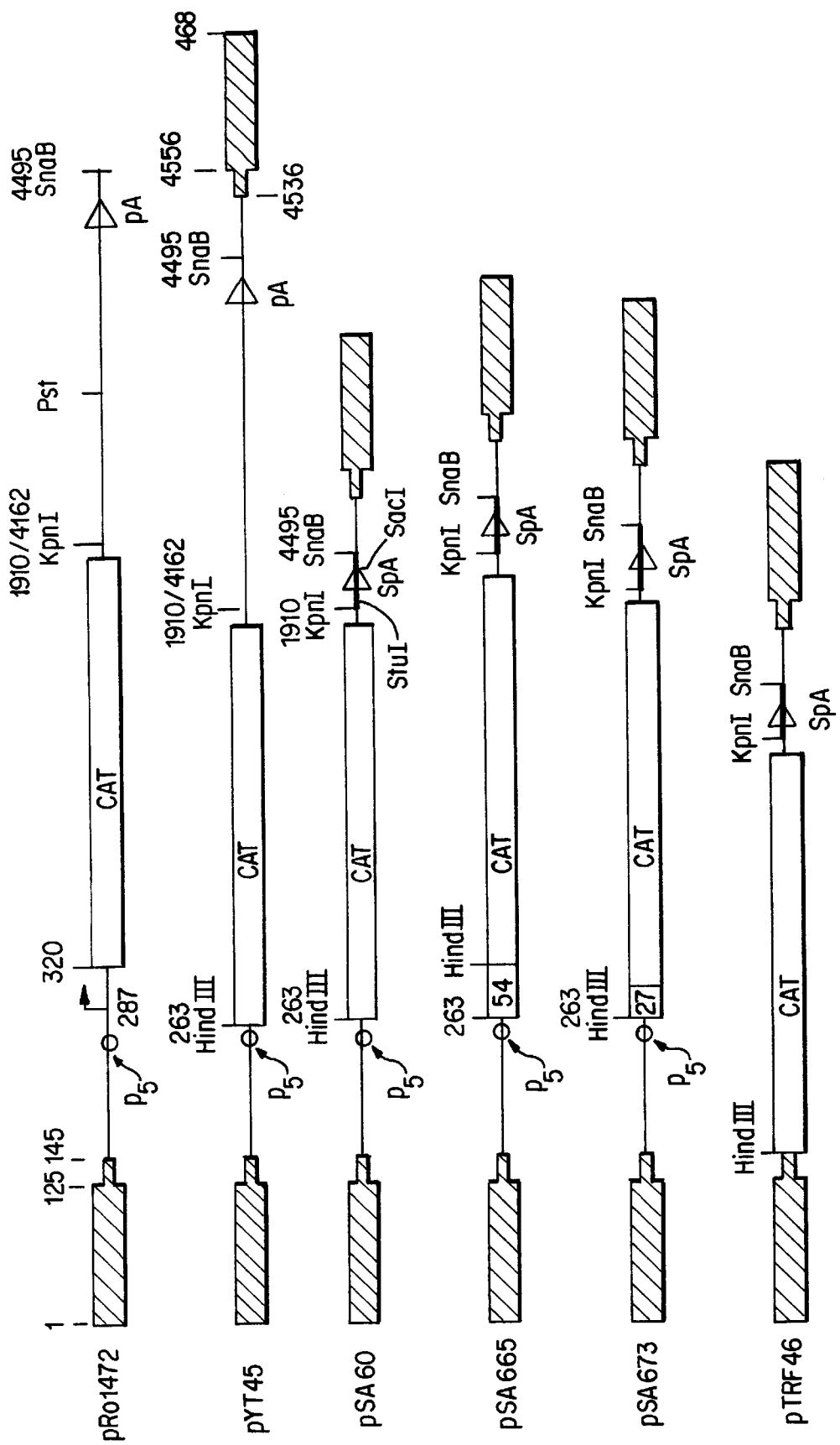
FIG. 1 shows the structure of AAV vector plasmids containing a cat coding sequence. pYT45 has the cat sequence inserted following nucleotides 1 to 263 of AAV and has the AAV poly A site. pRO45 was derived from pYT45 by deleting the right hand AAV ITR. pRO1472 contains the cat sequence inserted following the nucleotides 1 to 320 of the AAV genome and the AAV polyA site but is deleted for the right hand AAV ITR. pSA60was derived from pYT45 by deletion of the AAV polyA site and insertion of a synthetic polyA (SPA) site. pSA665 and pSA673 were derived from, pSA60 by insertion of a 54-mer or a 27-mer, respectively, comprising the sequences immediately upstream of the 5' start site of the cat cDNA coding sequence. pTRF46 contains the cat coding sequence inserted immediately following the left-hand AAV ITR sequence (AAV nucleotides 1 to 145), the synthetic polyA site and the right hand AAV ITR.

To test the efficiency of the AAV $p_5$ promoter in AAV vectors in human cells (Flotte et al., 1992) constructed several $p_5$ cat plasmids. The plasmid pRO1472 contains the cat coding sequence positioned immediately downstream of AAV nucleotides 1 to 321 (FIG. 1). This region of AAV includes several notable features including an AAV inverted terminal repeat (ITR) from AAV nucleotides 1 to 145 and the TATA box of the $p_5$ promoter at nucleotide 255. Nucleotides 204 to 213 constitute a binding site for the MLTF (USF) transcription factor and nucleotides 217 to 236 comprise a 10 bp repeat that constitutes a novel response element for the adenovirus transcription factor E1A (Chang et al., 1989). A previous report indicated that an AAV promoter consisting of nucleotides 190–310 had only minimal activity in HeLa cells unless activated by the E1A protein (Chang et al., 1989). In contrast, an AAV promoter comprising the nucleotides 145–310 had significant activity in HeLa cells in the absence of E1A (Beaton et al., 1989). These differences may reflect the presence, between nucleotides 160 to 180, of the sequence GTGACGTGAATTACGTCATAG [SEQ ID No:7], which has homology to the cAMP response element (CRE) and the binding site for the CREB/ATF transcription factor family (Hai et al., 1988; Montminy et al., 1990).

Flotte et al. (1992) examined several aspects of the AAV $p_5$ promoter vectors. The $p_5$-cat plasmid, pRO1472 was tested for cat expression after transfection into IB3 (airway epithelial) cells and CFPAC (pancreatic adenocarcinoma) cells and showed efficient cat expression. Furthermore, the activity of the $p_5$ promoter in pRO1472 was nearly 10-fold higher than that of the SV40 early promoter in pSV2CAT. The CRE element mediated a positive response to stimulation with forskolin to activate cAMP. These results suggested that, in the context of the entire left hand terminus of AAV in the complete $p_5$ promoter cAMP could mediate a modest induction of expression. The AAV $p_5$ promoter was also efficient for stable expression of a gene, neo, which mediates resistance to the antibiotic geneticin (gen$^r$) in mammalian cells. The plasmid $AAVp_5neo$ had neo expressed from a $p_5$ promoter similar to that in pRO1472 and was much more efficient than pSV2neo for gen$^r$ colony formation when transfected into IB3 cells. Also, when the $AAVp_5neo$ vector was packaged into AAV transducing particles and infected into cells up to 60 to 70 percent of the cells were transduced to the gen$^r$ phenotype. These experiments showed that the AAV $p_5$ promoter was efficient for integration and stable expression of a selective marker in human cells when used in AAV vectors.

Expression of a Gene from a Promoter Comprised Only of the AAV ITR

The experiments of Flotte et al. (1992), summarized above, showed that the AAV $p_5$ promoter could function well in AAV promoters and this is extremely useful. All AAV vectors that are to be used as AAV transducing vectors (i.e., by packaging into AAV particles) to promote efficient uptake must have an AAV ITR at each end of the packaged vector genome. That is because the ITR sequences contain all of the cis-acting sequence that is required for the AAV replication origin, for encapsulation of the genome into particles and for efficient integration into the host cell chromosome. In this context, the $p_5$ promoter is very useful because it forms a convenient cassette with the ITR region and adds only about 120 additional nucleotides. This helps to maximize the amount of space available for packaging foreign DNA into AAV vectors. These considerations are particularly important for encapsulation of larger genes or cDNAs which approach or exceed the packaging capacity of AAV as discussed above. As noted above, one such example is the CFTR cDNA which encodes the gene product which is responsible for the defect in the genetic disease cystic fibrosis.

In the course of constructing vectors that were designed to express genes such as CFTR from the AAV $p_5$ promoter, we inadvertently made one such plasmid construct in which the gene was inserted in the opposite direction. This vector plasmid would not have been expected to function because it did not have a known promoter in the correct orientation. However, due to a serendipitous mistake in a laboratory experiment, we tested this plasmid construct and discovered that it functioned to express the gene. This caused us to examine the construct carefully and we concluded that the ITR may be functioning as a transcription promoter. As a result, we performed specific experiments detailed in this specification which demonstrate that the ITR can act as a transcription promoter.

Thus, AAV vectors need have only the ITR sequences and a polyA site in order to express a foreign gene. This is a new and novel finding and indeed is against the expectation based on previously taught work, in which there was a commonly accepted agreement that the ITRs of AAV are not transcriptionally active (Walsh et al., 1992, PNAS [in press]). We show here that the AAV ITR is transcriptionally active in transient assays to express the cat gene and in stable integration assays to express a functional CFTR cDNA.

Construction of AAV Cat Vectors

FIG. 1 shows the construction of several AAV-cat vector plasmids. pRO1472 has the complete AAV $p_5$ promoter (nucleotide 145–263) and ITR (1–145) upstream of the cat gene as well as the AAV RNA start site (263–320) and the AAV polyA site downstream (KpnI/SnaB region). pSA60 has the polyA site deleted and replaced with a smaller synthetic polyA site which increases the packaging capacity of the vector. This polyA site also has an additional property that it is translationally open in the reverse orientation (i.e, reading from the right hand ITR). In pSA665 and pSA673, respectively, an additional 54 or 27 nucleotides, derived from the CFTR cDNA sequence immediately upstream of the presumptive CFTR initiation codon, is inserted immediately upstream of the cat gene. In pTRF46, the cat gene is inserted immediately following the AAV ITR sequence.

These AAV-cat plasmids were transfected into human (293) cells and cat activity was measured in extracts prepared 48 hr later. As shown in Table I, pRO1472 efficiently expressed cat. Also, the plasmid, pSA60, having a full $p_5$ promoter and a synthetic polyA site was as efficient as pRO1472. pSA665 and pSA673 were about 1.5 fold more efficient presumably because the AUG initiation codon for the cat coding region was moved away from the immediate proximity of the 5' cap region of the mRNA as compared to pSA60. Surprisingly, pTRF46, expressed cat as efficiently as pRO1472 or pSA60, even though it contains none of the previously characterized $p_5$ promoter (i.e., nucleotides 145 to 320). This shows that the AAV ITR sequence is itself capable of acting as an efficient promoter for gene expression. This is an unprecedented and novel finding for AAV that this region is also a promoter.

TABLE I

EXPRESSION OF GENE ACTIVITY FROM AAV VECTORS

| Vector[a] | Cat Activity (%)[b] |
|---|---|
| pR01472 | 27.5 |
| pSA60 | 28.2 |
| pTRF46 | 26.6 |
| pSA665 | 43.1 |
| pSA673 | 40.1 |
| control | 0.02 |

[a]human 293 cells ($10^6$ cells per 35 mm dish) were transfected with 5 µg of the indicated vector plasmid. The control culture was not transfected.
[b]48 hr after transfection cell lysates were prepared and cat activity was measured as the amount (%) of $^{14}$C-Chloramphenicol which was acetylated by incubation with 20 µL of lysate (equivalent to 1.3 × $10^5$ cells) at 37° C. for 1 hr followed by separation of the acetylated and unacetylated substrate by silica-gel thin-layer chromatography and scintillation counting to determine radioactivity.

Construction of AAV-CFTR Vectors

FIG. 2 shows several AAV-CFTR vectors designed to express CFTR either from the AAV $p_5$ promoter as in pSA313 or from the AAV ITR as in pSA313 or pSA306. In pSA313, the CFTR cDNA of 4500 nucleotides is inserted downstream of the AAV promoter analogous to that in pSA60, i.e, AAV nucleotides 1 to 263, at the left. In pSA315 the CFTR cDNA was inserted in the opposite orientation such that it is downstream of the right-hand AAV ITR sequence and the synthetic polyA site. In this configuration the CFTR is expressed from the right-hand ITR and the polyA site can be read through translationally in the reverse direction as noted above. In pSA306, the construct is exactly analogous to pSA315 except that 350 nucleotides of the amino terminal region of CFTR cDNA have been deleted. This results in expression from the right-hand ITR of a fusion protein consisting of a N-terminally deleted CFTR protein having a fusion region at its N-terminus derived from reading through the synthetic polyA site in the reverse direction i.e., from right to left in the orientation of FIG. 2.

The plasmid pSA464 is a control derived from pSA306 by introducing a frameshift mutation such that it can not produce a functional CFTR protein.

Expression of CFTR and Complementation of the CF Defect in Stable Transfectants of CF Airway Cells To examine the efficiency of the AAV-CFTR vectors for expression of the CFTR gene, the plasmids shown in FIG. 2 were each transfected using cationic liposomes (Lipofectin Reagent, BRL, Gaithersburg, Md.) into IB3 cells, together with pAAVp$_5$neo. Control cells were transfected with pAAVp$_5$neo alone. Gen$^r$ colonies were picked from the original plates and expanded into stable cultures and characterized for functional expression of the CFTR protein. All of these clones were stable for neo expression during repeated passage over several months in culture.

Figure 3A:
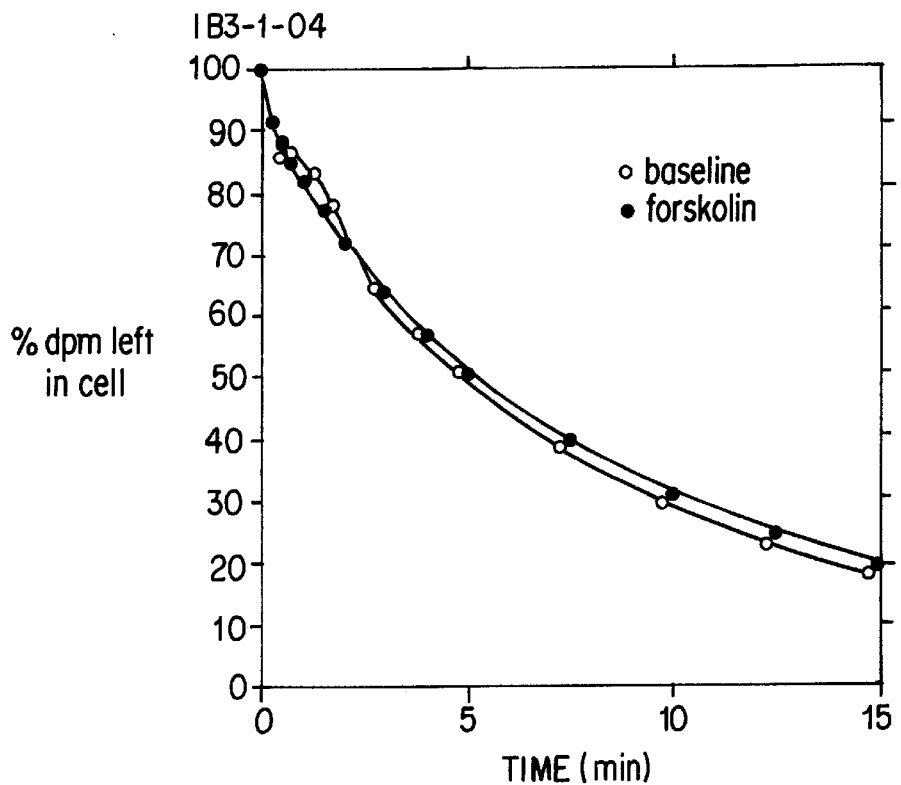
Figure 3B:
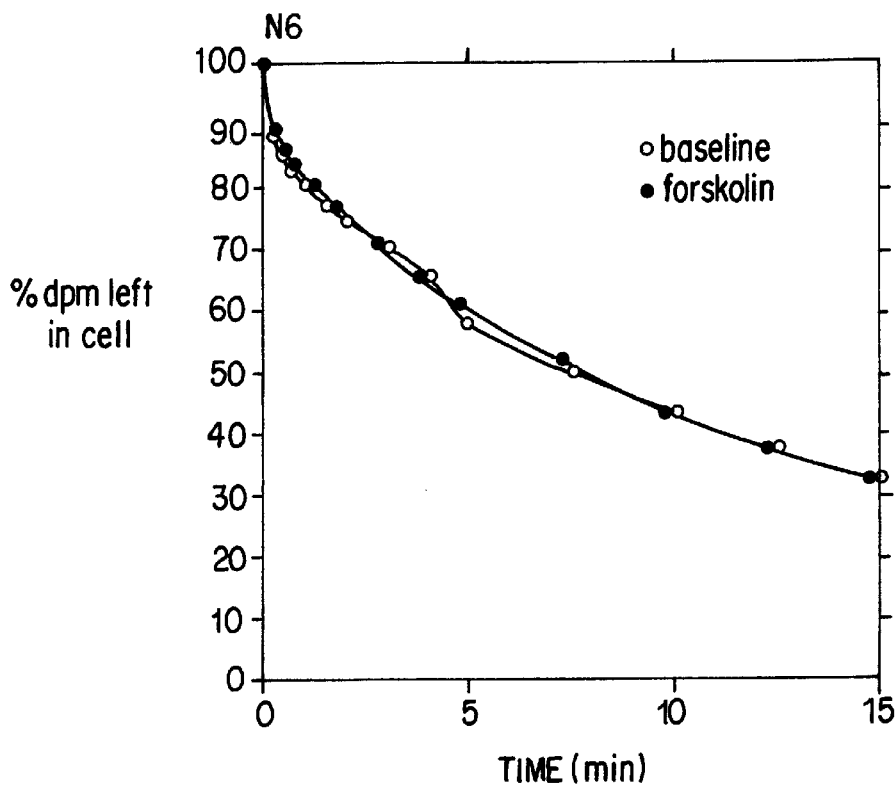
Figure 3C:
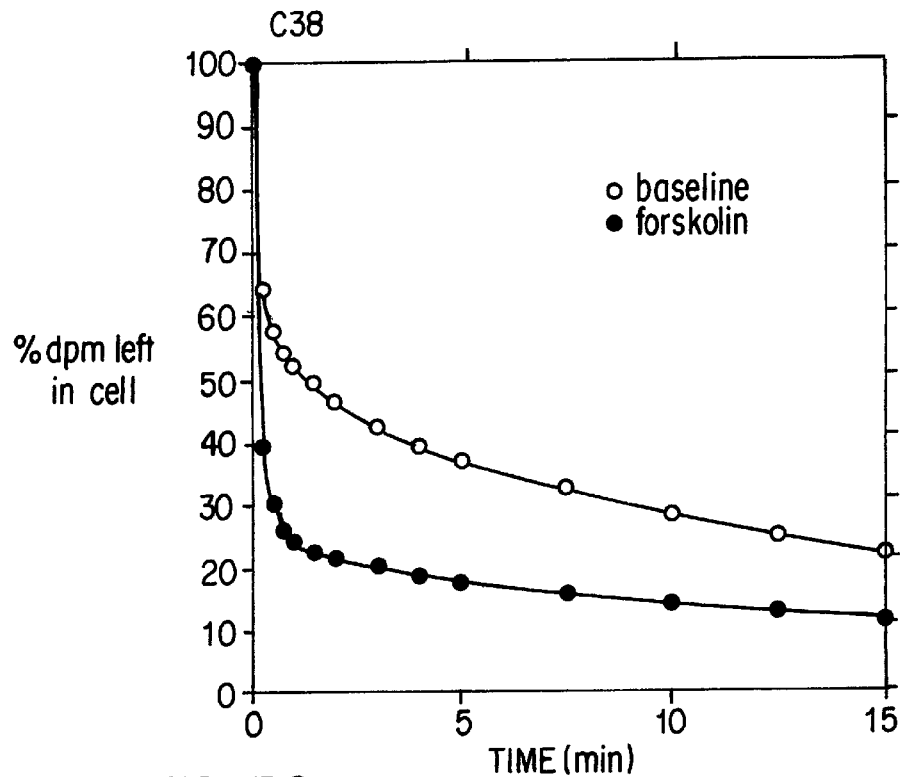
Figure 3D:
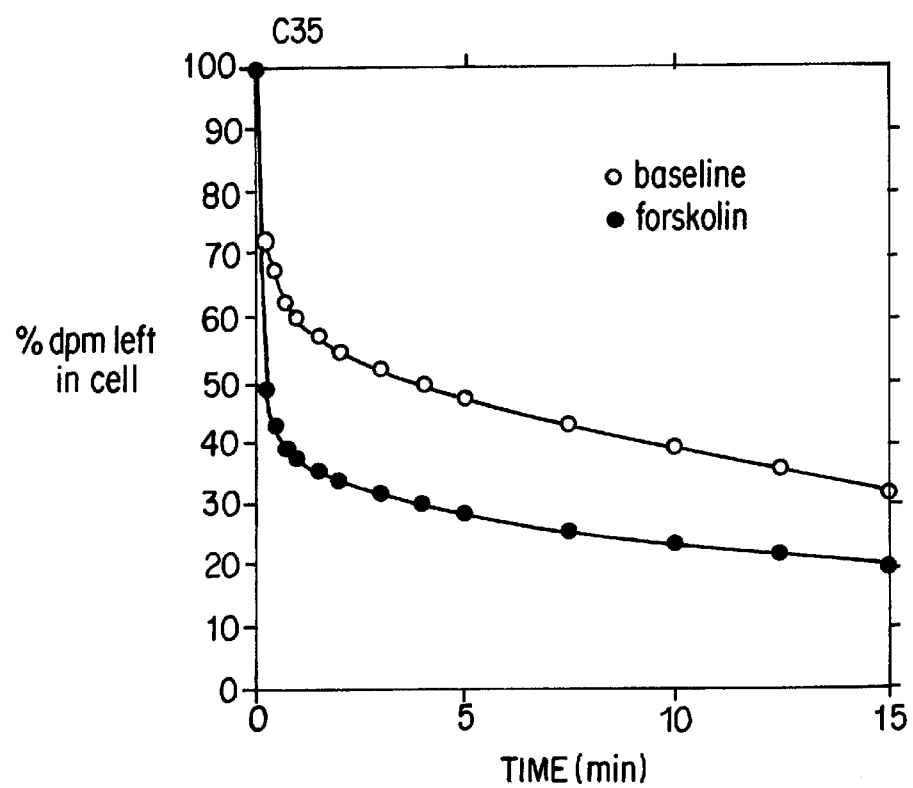

Expression of CFTR can Be Detected in Functional Assays in IB3 Cells Which Have the Cystic Defect A functional CFTR protein should restore to these cells a Cl$^-$ conductance which is regulated by cAMP and thus is stimulated by forskolin (Drumm et al., 1990, Cell 62:1227–1233, Hwang et al., Science 244:1351–1353; Li et al., 1988, Nature (London) 331:358–360; Li et al., 1989, Science 244:1353–1356; Rich et al., 1990, Nature 347:358–363). Examples of Cl$^-$ efflux are shown in FIG. 3 and a summary of the rate constants calculated from this data are shown in FIG. 4. Both the parental IB3 cells and the control N6 clone (transfected with pAAVp$_5$neo alone) exhibited a relatively slow Cl$^-$ efflux rate that was not responsive to forskolin (FIGS. 3A and 3B). In contrast, a number of the clones of AAV-CFTR transfectants, as shown in FIG. 3 for clones C35 (FIG. 3D) and C38 (FIG. 3C) (both derived from transfection of pSA306), exhibited significantly increased basal rates of efflux but more significantly showed the characteristic additional increase in efflux in response to forskolin.

As shown in the summary (FIG. 4) 28% (4/14) of the pSA313 transfectants, and 50% (6/12) of the transfectants with either pSA315 or pSA306 were complemented for the defect. This shows that all three vector constructs were functional. The increased number of functional clones with pSA313 or pSA306 may indicate that the ITR promoter in the vectors was more efficient than the p$_5$ promoter in pSA313. None of the clones transfected with the control vector pSA464 were complemented. These results show two novel findings. First, the AAV ITR sequence functions efficiently also as a promoter when stably integrated into cells as shown by the function of both pSA313 and pSA306. Second, the truncated CFTR protein expressed from pSA306 is also functional for complementation of the CFTR defect. In the pSA306 vector the largest open reading frame expresses a fusion protein by reading through most of the synthetic polyA sequence in the reverse direction.

The observations with pSA306 are especially pertinent because it was taught previously that the region of CFTR that is deleted in pSA306 was in fact essential for CFTR function when CFTR is expressed from various others vectors such as vaccinia (Andersen et al., 1991, Science 251:679–682). Also, the overall size of the AAV-CFTR vector in pSA306 is equivalent to the size of wild type AAV DNA and thus this vector should be packageable into AAV particles to use as a transducing vector. We examined packaging of the pSA306 vector into AAV particles. To examine packaging of AAV-CFTR vector pSA306 into AAV particles adenovirus-infected 293 cells were transfected with the AAV-CFTR vector (pSA306) in the presence (+) or absence (-) of the AAV packaging plasmid (pAAV/Ad). Lysates of the cultures were prepared 72 hr after transfection and used to infect fresh cultures of adenovirus-infected 293 cells in the absence (minus wt) or presence (plus wt) of added wild type AAV particles (m.o.i 3). 40 hr after infection, Hirt lysates of the cells were prepared and viral DNA was electrophoresed in an agarose gel, blotted to nitrocellulose, and hybridized with a CFTR $^{32}$P-DNA probe specific for the SA306 vector (306) or with AAV $^{32}$P-DNA probe specific for wild-type AAV (AAV). Replication of the SA306 vector was only detected in lysates that had been packaged in the presence of pAAV/Ad and were subsequently infected in the presence of added wild-type AAV particles. This showed that the AAV-CFTR vector could be packaged into AAV transducing particles.

To demonstrate the functionality of the SA306 AAV-CFTR transducing vector IB3 cell cultures were infected with vector preparations containing packaged SA306 or a control SA464 vector at a multiplicity of 400 vector particles per cell. The cultures were grown several weeks in culture and assayed for functional expression of the CFTR. As shown in FIG. 5, the culture infected with the SA306 vector (A0 cells) was functionally complemented for the CF defect as shown by the response to forskolin. In contrast the control culture infected with the control SA464 vector (2F2 cells) was not complemented as shown by the lack of response to forskolin.

The results shown in FIGS. 3, 4, and 5 have been confirmed by other functional assays including immunofluorescent detection of the CFTR protein and electrophysiological assays using patch-clamp techniques.

The results described above demonstrate complementation and stable correction of the CF defect in airway epithelial cells after cationic liposome mediated transfection with AAV-CFTR vector or after infection of the cells with AAV-CFTR transducing vector particles. These results demonstrate the utility of the AAV vectors and the invention as practiced with AAV vectors using an ITR as the promoter and incorporating a synthetic polyA site having special features.

Our studies with the AAV-CFTR vectors were performed as an initial step in evaluating the feasibility of using an AAV vector for gene therapy. In this respect it is important that we have demonstrated stable complementation of the CF defect in cells derived from bronchial epithelium since this the site of the major clinical manifestation of the disease and is the most likely site for targeting of gene therapy vectors. The complementation experiments reported with a retroviral vector (Drumm et al., 1990, Cell 62A:1227–1233) were performed in CFPAC cells which are pancreatic cells rather than airway cells.

Expression of CFTR in vivo

AAV vectors, especially those expressing a gene from the ITR, can be used to treat human patients in the following general way. If the vector is to be delivered as transducing particles, it can first be packaged into AAV particles, in the general way described here for the AAV-CFTR vector SA306, or using any other suitable packaging system. The AAV transducing vector can be purified to remove and/or inactivate any adventitious agents or toxic compounds by banding in CsCl or any other appropriate procedure. For AAV vectors expressing a functional CFTR gene, or any other gene for treating a pulmonary disease, the vector can be delivered directly in vivo to the lung either by intubation and bronchoscopy or by a nebulizer or by a nasal spray or by inhalation as an appropriate formulation of nose drops. For this or other diseases, the AAV vector particles can be delivered in vivo by intravenous or enteric administration or perhaps subcutaneously.

The vector can also be used in ex vivo gene therapy procedures by removal of cells from a patient that is then infected with the AAV vector particles and the cells are returned to the patient after a period of maintenance and/or growth ex vivo.

The AAV vectors can also be administered in either in vivo or ex vivo gene therapy procedures in various other formulations in which the vector plasmid is administered as free DNA either by direct injection or after incorporation into other delivery systems such as liposomes or systems designed to target by receptor-mediated or other endocytosis procedures. The AAV vector can also be incorporated into an adenovirus, retrovirus or other virus which can be used as the delivery vehicle.

Other Vectors Utilizing the Promoter Region Sequences from ITR

An additional use of the present discovery is to utilize the sequences of ITR which are responsible for promotion in other vectors. The ITR region of AAV does not have a normal TATA motif common to many eukaryotic promoters and was not previously recognized to function within the context of an AAV genome as a transcription promoter. It is likely that in the context of the AAV genome this ITR does not function as a promoter perhaps because of effects of the other known AAV promoters downstream of this. However, not all eukaryotic transcription promoters require or possess the TATA motif. After we demonstrated that the AAV ITR functions as a promoter we examined the ITR sequence for elements that are likely to explain this function.

Inspection of the ITR sequence shows two motifs that are likely to be important in its function as a promoter. First, in the region between AAV nucleotide 125 and 145 (commonly known as the AAV d sequence) there is the sequence 5'-AACTCCATCACT-3' [SEQ ID NO8]. This is only one base different from similar sequences at the 5' start site of the promoters for human terminal deoxynucleotidyl transferase gene and for the adenovirus major late gene promoter and matches closely the consensus sequence for an element described as an Inr (Initiator) element (Smale, S. T. and Baltimore, D., 1989, Cell 57:103–113; Smale et al., 1990, Proc. Natl. Acad. Sci. U.S.A. 87:4509–4513). A second series of GC-rich elements is present in the ITR region between nucleotides 1 and 125 including the elements, GGCCGCCCGGGC [SEQ ID NO9] from nucleotides 41 to 50, AAAGCCCGGGCGTCGGGCGACC [SEQ ID NO10] from nucleotides 51 to 73, GGTCGCCCGGCCTCA [SEQ ID NO11] from nucleotides 76 to 90, and CAGCGGC-GAGAG [SEQ ID NO12] from nucleotides 101 to 112 which have strong homology with the series of consensus sites shown to be sites for the common transcription factor Sp1 (Pitluck and Ward, 1991, J. Virol. 65:6661–6670). Finally, it is now known that an Inr sequence in the presence of sites for other factors such as Sp1 can function as a transcription promoter (Smale and Baltimore, 1989; Smale et al., 1990).

It is likely that these or other regions of the ITR may be important in allowing it to function as a transcription promoter. It is now straightforward and obvious to others experienced in the field to perform standard mutagenesis techniques to alter the ITR sequence (for instance, in the context of the plasmid pTRF46) to determine precisely the controlling elements and to modulate the transcriptional activity of the ITR either up or down.

Throughout this application various publications are referenced. The disclosures of these publications in their entireties are hereby incorporated by reference into this application in order to more fully describe the state of the art to which this invention pertains.

Although the present processes have been described with reference to specific details of certain embodiments thereof, it is not intended that such details should be regarded as limitations upon the scope of the invention.

What is claimed is:

1. A method for transducing a cell with a modified adeno-associated viral vector comprising introducing into the cell a polynucleotide comprising the inverted terminal repeat sequences of adeno-associated virus and a nucleic acid, wherein the inverted terminal repeat sequences promote expression of the nucleic acid, in the absence of another promoter functionally linked to the nucleic acid.

2. The method of claim 1, comprising transfecting the cell with the modified adeno-associated viral vector.

3. The method of claim 1, comprising infecting the cell with the modified adeno-associated viral vector.

4. The method of claim 1, wherein the nucleic acid encodes a polypeptide.

5. The method of claim 1, wherein the cell is human.

6. The method of claim 4, wherein the polypeptide is a functional protein.

7. The method of claim 6, wherein the protein is a cystic fibrosis transmembrane conductance regulator.

* * * * *